United States Patent

Ngooi et al.

[11] Patent Number: 5,338,871
[45] Date of Patent: Aug. 16, 1994

[54] PREPARATION OF FORM 1 RANITIDINE HYDROCHLORIDE

[75] Inventors: Teng-Ko Ngooi, Scarborough; Jeffry D. McGolrick; Casimir Antczak, both of Aurora; James L. A. Tindall, Goodwood, all of Canada

[73] Assignee: Torcan Chemical Ltd., Aurora, Canada

[21] Appl. No.: 41,354

[22] Filed: Apr. 1, 1993

Related U.S. Application Data

[63] Continuation of Ser. No. 811,143, Dec. 20, 1991, abandoned.

[51] Int. Cl.$^5$ .......................................... C07D 307/52
[52] U.S. Cl. ................................................. 549/492
[58] Field of Search ........................................ 549/492

[56] References Cited

U.S. PATENT DOCUMENTS

| | | | |
|---|---|---|---|
| 4,460,506 | 7/1984 | Bradshaw | 549/492 |
| 4,551,548 | 11/1985 | Kleemann et al. | 562/402 |
| 4,613,688 | 9/1986 | Inoue et al. | 562/402 |
| 5,075,301 | 12/1991 | Sasho et al. | 549/492 |

Primary Examiner—C. Warren Ivy
Assistant Examiner—A. A. Owens
Attorney, Agent, or Firm—Ridout & Maybee

[57] ABSTRACT

Pure Form 1 ranitidine hydrochloride is prepared by a process of crystallization from a solution of ranitidine hydrochloride in a mixed solvent comprising 1 part by volume of at least one lower alkanol such as ethanol and 1–2.0 parts by volume of a $C_6$–$C_{10}$ aromatic hydrocarbon such as toluene, and in the presence of seed crystals of pure Form 1 ranitidine hydrochloride. In the preferred process according to the invention, the ranitidine hydrochloride is prepared in situ in the solvent mixture by adding hydrochloric acid to a solution of the free base in the solvent mixture, in the presence of the seed crystals.

9 Claims, No Drawings

PREPARATION OF FORM 1 RANITIDINE HYDROCHLORIDE

This application is a continuation of application Ser. No. 07/811,143, filed Dec. 20, 1991, now abandoned.

FIELD OF THE INVENTION

This invention relates to the pharmaceutical chemical compound known as ranitidine hydrochloride, and to processes for its preparation and isolation in a specific crystalline form.

BACKGROUND

Ranitidine is, chemically, N-[2-[[[5-[(dimethylamino)-methyl]-2-furanyl]methyl]thio]ethyl]-N'-methyl-2-nitro-1,1-ethene diamine, and has the chemical structural formula:

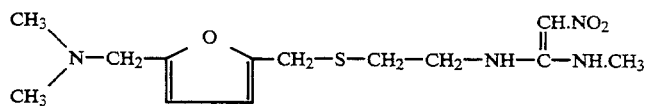

In the form of its hydrochloride salt, ranitidine has achieved widespread acceptance as a medicament for treating ulcers.

The patent and technical literature concerning ranitidine hydrochloride reports that it exists in two different crystalline forms, Form 1 and Forth 2. The preparation and characteristics of ranitidine hydrochloride Form 2, which is the commercially marketed form, are described in Canadian Patent no. 1,202,638 Crookes, assigned to Glaxo Group Limited, and issued Apr. 1, 1986. In this patent disclosure, ranitidine hydrochloride Form 1 is reported to be formed by precipitation and crystallization from a solution of ranitidine in industrial methylated spirit containing hydrogen chloride, by addition of ethyl acetate thereto. It is also reported therein that Form 1 ranitidine hydrochloride so produced has unsuitable filtration and drying characteristics, and that Form 2 ranitidine hydrochloride has more advantageous properties, and better characteristics from a manufacturing point of view. This Form 2 ranitidine hydrochloride is reportedly obtained by appropriately chosen crystallization processes. One of these is dissolving the free base in a hydroxylic solvent such as propan-2-ol and treating the solution with hydrochloric acid, followed by crystallization at an elevated temperature by adding further quantities of propan-2-ol. Another is dissolving Form 1 ranitidine hydrochloride in methanol or ethanol with warming, followed by cooling to cause crystallization of the Form 2 salt, optionally accompanied by the addition of an anti-solvent or accompanied by seeding with Form 2 ranitidine hydrochloride crystals.

SUMMARY OF THE INVENTION

The present invention provides a novel crystallization process for the production of Form 1 ranitidine hydrochloride. Whereas Form 2 ranitidine hydrochloride is generally formed on precipitation and crystallization from alcohol, it has been found according to the present invention that, if ranitidine hydrochloride is crystallized from a solution comprising a mixture of one or more lower aliphatic alcohols and an aromatic hydrocarbon within a certain range of relative proportions of the solvents, and the solution is seeded with crystals of pure Form 1 ranitidine hydrochloride, then Form 1 ranitidine hydrochloride is obtained in pure form, as determined by IR and powder x-ray diffraction analysis. Moreover, the Form 1 ranitidine hydrochloride produced according to this invention has good filtering and drying characteristics.

Thus according to the present invention, there is provided a process for preparing Form 1 ranitidine hydrochloride, which comprises forming a solution of ranitidine hydrochloride in a mixed solvent comprising at least one $C_1$–$C_4$ alkanol and a $C_6$–$C_{10}$ aromatic hydrocarbon, the volume ratio of alkanol(s) to hydrocarbon being from about 1:1 to 1:2, and initiating crystallization of Form 1 ranitidine hydrochloride from said solution in the presence of seed crystals of pure Form 1 ranitidine hydrochloride.

DESCRIPTION OF THE PREFERRED EMBODIMENTS

The preferred aromatic hydrocarbon for use in the present invention is toluene.

Ranitidine free base is freely soluble in lower alkanols, but the hydrochloride salt thereof is only sparingly soluble in alkanols at room temperature. Accordingly, a preferred manner of operation according to the present invention is to make a solution of the free base in the mixed solvent and add to that solution an appropriate quantity of hydrochloric acid, preferably as a solution in a lower alkanol such as one chosen as part of the mixed solvent system, so as to form the ranitidine hydrochloride salt in situ in solution in the mixed solvent. Suitable amounts of acid are from about 0.8 to about 1.15 equivalents, and most preferably from 0.95 to 1.0 equivalents, per equivalent of free base. As the hydrochloride salt is formed in solution, in the presence of the seeding crystals of Form 1 ranitidine hydrochloride, crystallization of Form 1 ranitidine hydrochloride occurs. The crystallization can be assisted by agitation of the solution and by cooling, as the hydrochloride salt is formed.

Preferred alkanols for use in the present invention are ethanol and isopropanol, with ethanol being most preferred.

The formation of the hydrochloride salt of ranitidine from the free base is an exothermic reaction, and is accompanied by an increase in the viscosity of the solution. It is accordingly preferred to dilute the solution with more of a similar solvent mixture or isopropanol as the reaction proceeds, so that it can be properly agitated. The specified volumetric ratio of solvents thus refers to that present at the initiation of crystallization. Once crystallization has commenced, pure Form 1 ranitidine continues to crystallize, even though dilution may cause the volumetric ratio of the mixed solvents to vary from that specified above. It is preferred to operate near room temperatures and to avoid causing a rise in temperature at any time above about 40° C.

It is also preferred according to the present invention to conduct a washing step on the final, crystallized product, using isopropanol. At room temperatures and below, Form 1 ranitidine hydrochloride is substantially insoluble in isopropanol. Washing with isopropanol at this stage leads to significant colour improvement in the product formed according to this process.

It is of course best to conduct the process with substantially water-free reagents and solvents, and under inert atmospheres, such as under a blanket of nitrogen.

The invention will be further described, for illustrative purposes, with reference to the following specific examples.

DESCRIPTION OF THE MOST PREFERRED EMBODIMENTS

Example 1

All the steps in the procedure were conducted under a nitrogen atmosphere, and all the reagents and solvents were effectively water-free.

106 g (85% purity, 0.29 mole) of ranitidine free base was dissolved in 130 ml ethanol and diluted with 240 ml toluene under a constant flow of nitrogen. With mechanical stirring, the solution was seeded with pure Form 1 ranitidine hydrochloride crystals, and then a solution of 32 ml (0.29 mole) of 8.9M hydrochloric acid in ethanol was added at room temperature. The reaction mixture was stirred until a viscous suspension resulted, and this was diluted with 50 ml of a 1:1.5 mixture of ethanol/toluene. After stirring for one hour, 200 ml of isopropanol was added. The mixture was stirred for another hour and filtered. The filter cake was washed with 3×100 ml isopropanol, and dried and vacuumed at 50° C. to give 95 g (90%) of off-white product. IR analysis confirmed it to be pure Form 1 ranitidine hydrochloride.

Example 2

A solution of 50 ml of hydrochloride acid in ethanol containing 9.5 g HCL (0.26 mole) was added to a solution of 100 g (85% purity, 0.27 mole) of ranitidine free base in 525 ml of a 1:2 mixture of ethanol/toluene in the presence of Form 1 ranitidine hydrochloride crystals at room temperature. After stirring for one hour, 100 ml of 1:1.5 mixture of ethanol/toluene was added. After another hour, 200 ml of isopropanol was added. The slurry was stirred for another hour and filtered. The filter cake was washed with isopropanol to give 85 g of off-white solid which was confirmed by IR and powder x-ray diffraction analysis to be pure Form 1 ranitidine hydrochloride.

Example 3

45 g (0.14 mole) of crude ranitidine free base was dissolved in 102 ml of isopropanol under an atmosphere of nitrogen and then diluted with 150 ml of toluene. The solution was cooled to 10° C. with an ice bath. Then Form 1 ranitidine hydrochloride crystals were added, followed by 47.6 ml (10 mole) of 2.12M HCL in isopropanol was added. The product started to oil out. The mixture was agitated overnight and the solid formed was filtered, and the filter cake was washed with 500 ml isoproponal. Drying at 50° C. under vacuum gage 32 g (65%) of pure Form 1 ranitidine hydrochloride.

What is claimed is:

1. A process for preparing Form 1 ranitidine hydrochloride, which comprises:
   forming a solution of ranitidine hydrochloride in a mixed solvent comprising at least one $C_1$–$C_4$ alkanol and a $C_6$–$C_{10}$ aromatic hydrocarbon, the volume ratio of alkanol(s) to hydrocarbon being from about 1:1 to 1:2;
   and initiating crystallization of Form 1 ranitidine hydrochloride from said solution in the presence of seed crystals of pure Form 1 ranitidine hydrochloride.

2. The process of claim 1, including the preliminary step of adding hydrochloric acid to a solution of ranitidine free base or soluble salt thereof in said mixture of solvents.

3. The process of claim 2, wherein the hydrochloric acid is added in an amount of from about 0.8 to 1.15 molar equivalents of acid per molar equivalent of free base.

4. The process of claim 3, wherein the hydrochloric acid is added in an amount of from about 0.95 to 1.0 molar equivalents of acid per molar equivalent of free base.

5. The process of claim 4, wherein the aromatic hydrocarbon is toluene.

6. The process of claim 5, wherein the alkanol is ethanol or isopropanol, or a mixture thereof.

7. The process of claim 6, wherein the volume ratio of alkanol(s) to toluene at the initiation of crystallization is about 1:1.5.

8. The process of claim 7, including the additional and subsequent step of washing the Form 1 ranitidine hydrochloride so formed with isopropanol.

9. The process of claim 8, wherein the alkanol is ethanol.

* * * * *